United States Patent [19]

Grollier

[11] Patent Number: 4,582,702

[45] Date of Patent: Apr. 15, 1986

[54] CLEANING PRODUCT FOR DENTAL AND ORAL CARE, CONTAINING A NON-IONIC POLY(HYDROXYPROPYL ETHER) SURFACE-ACTIVE AGENT

[75] Inventor: Jean F. Grollier, Paris, France

[73] Assignee: L'Oreal, Paris, France

[21] Appl. No.: 615,828

[22] Filed: May 31, 1984

[30] Foreign Application Priority Data

May 31, 1983 [LU] Luxembourg .............................. 84833

[51] Int. Cl.$^4$ ............................ A61K 7/18; A61K 7/16
[52] U.S. Cl. ............................................. 424/52; 424/49
[58] Field of Search .................... 424/49, 70, 73, 52; 252/DIG. 1; 514/835, 901

[56] References Cited

U.S. PATENT DOCUMENTS 3,578,719 5/1971 Kalopissis et al. ...................... 424/63
3,821,372 6/1974 Vanlerberghe et al. ............... 568/46
4,150,151 4/1979 Pader et al. ............................ 424/49
4,307,079 12/1981 Zorayan et al. ....................... 424/47
4,376,763 3/1983 Barth et al. ............................ 424/49
4,393,042 7/1983 Battista .................................. 424/49
4,465,661 8/1984 Schmolka .............................. 424/49

FOREIGN PATENT DOCUMENTS 2169787 9/1973 France .

Primary Examiner—Ronald W. Griffin
Attorney, Agent, or Firm—Fleit, Jacobson, Cohn & Price

[57] ABSTRACT

A cleaning product for dental, gum and oral care, in particular a toothpaste or mouthwash, characterized in that it contains a non-ionic poly(hydroxypropyl ether) surface-active agent in a proportion of 0.1 to 4% of the total weight of the cleaning product.

The non-ionic poly(hydroxypropyl ether) surface-active agents have a good compatibility with cationic anti-plaque bactericides, have a good foaming power, do not attack the mucous membranes and, at the percentages employed, do not have an unpleasant taste.

16 Claims, No Drawings

CLEANING PRODUCT FOR DENTAL AND ORAL CARE, CONTAINING A NON-IONIC POLY(HYDROXYPROPYL ETHER) SURFACE-ACTIVE AGENT

The invention relates to a cleaning product for dental and oral care, and more particularly a toothpaste or a mouthwash, containing a non-ionic poly(hydroxypropyl ether) surface-active agent.

The purpose of cleaning products for dental and oral care is to clean the teeth and the mouth and to prevent the formation of dental plaque, which is caused by bacteria.

Dental plaque is a deposit formed on the teeth and the gums. It consists of food debris and especially carbohydrates. It must be removed quickly; otherwise it hardens and adheres strongly. Dental plaque also contains bacteria and assists their multiplication. These bacteria secrete acid products capable of attacking the tooth enamel.

The bacterial activity which is present in dental plaque is considered to be the essential cause of dental caries. Likewise, the dental plaque existing in the interstices between the teeth and the gums and on the gums themselves plays a considerable part in gum complaints.

Cleaning products in the form of a paste for dental care contain two main constituents:

a water-insoluble abrasive powder for removing the film of dirt, containing good debris in particular, which deposits on the teeth, in the interstices between the teeth and the gums and also on the gums; and a surface-active agent, the purpose of which is to assist in removing the film of dirt and the dental plaque.

To be able to perform this function satisfactorily, the surface-active agent must fulfill several conditions:

(a) assist in penetrating and detaching the film of dirt covering the teeth and the gums, and in suspending it in the toothpaste;

(b) have an adequate foaming power;

(c) not attack the mucous membranes;

(d) not have an unpleasant taste; and (e) be compatible with the other constituents of the toothpaste or mouthwash.

The surface-active agents which best fulfil these conditions (a), (b), (c) and (d) are anionic surface-active agents, sodium lauryl-sulphate being the one most commonly used.

However, anionic surface-active agents have the disadvantage that they are not easily compatible with the bactericidal anti-plaque substances generally present in toothpastes or mouthwashes. In the majority of cases, these substances are nitrogen bases or their salts of cationic type.

In fact, when anionic surface-active agents are mixed with cationic substances, there is a risk of deactivation.

Attempts have been made to overcome this disadvantage by effecting dental and oral care using products consisting of two separate compositions, one of the compositions containing the anionic surface-active agent and the other composition containing the cationic bactericidal anti-plaque substance. This type of product consisting of two separate compositions is described in French Pat. No. 2,282,861.

However, this type of composition containing two constituents has disadvantages in terms of packaging and its use is complicated and not readily acceptable to the consumer.

It has also been proposed to replace the anionic surface-active agent with non-ionic, cationic or amphoteric surface-active agents. The non-ionic surface-active agents proposed for use in toothpastes and mouthwashes are essentially condensation products of ethylene oxide with various organic substrates, if appropriate in association with propylene oxide or butylene oxide.

Unfortunately, a surface-active agent other than anionic which has a sufficient efficacy without the disadvantage of a marked bitter taste when used has not yet been found.

The Applicant Company has discovered that certain non-ionic surface-active agents belonging to the class of the poly(hydroxypropyl ethers) make it possible to replace the anionic surface-active agents, compared with which they have the advantage of good compatibility with cationic bactericidal anti-plaque substances.

These poly(hydroxypropyl ethers) have a better foaming power than the other non-ionic surface-active agents. Furthermore, they do not attack the mucous membranes.

The invention consequently relates to a cleaning product for dental and oral care, which is more particularly in the form of a toothpaste or a mouthwash, characterized in that it contains a non-ionic poly(hydroxypropyl ether) surface-active agent.

The invention also relates to the use of the non-ionic poly(hydroxypropyl ether) surface-active agents in toothpastes, mouthwashes and other compositions capable of being used for dental care, gum care and oral care in general. Other objects of the invention will become apparent on reading the description and the examples.

The non-ionic poly(hydroxypropyl ether) surface-active agents to be used in the cleaning products for dental and oral care according to the invention are chosen from the compounds of the formulae (I) and (II) below and/or from the compounds prepared by the process described in paragraphs (ii) and (iv) below:

(i)

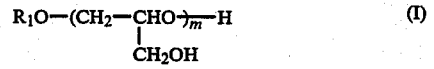

in which $R_1$ denotes an alkyl radical containing 10 to 14 carbon atoms, or a mixture of such alkyl radicals, and m is an integer or decimal number from 2 to 10 and preferably from 3 to 6. These compounds of the formula (I) can be prepared by the process described in French Pat. No. 1,477,048 or U.S. Pat. No. 3,578,719;

(ii) compounds prepared by the condensation, under alkaline catalysis, of 2 to 10 mol, and preferably of 2.5 to 6 mol, of glycidol with a $C_{10}$–$C_{14}$ alpha-diol, or a mixture of such alpha-diols, at a temperature of 120°–180° C. and preferably of 140° to 160° C., the glycidol being added slowly.

The preparation of the above compounds is described with full details in French Pat. No. 2,091,516 or in U.S. Pat. No. 3,821,372; U.S. Pat. No. 3,821,372;

(iii)

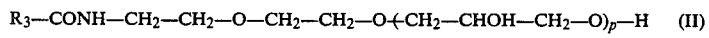

in which $R_3$ denotes an alkyl and/or alkenyl radical having from 11 to 18 carbon atoms, or a mixture of such alkyl and/or alkenyl radicals, and p denotes an integer or decimal number from 1 to 5 and preferably from 1.5 to 4. These compounds of the formula (III) can be prepared by the process described in French Pat. No. 2,328,763 or according to U.S. Pat. No. 4,307,079;

(iv) the compounds prepared by the condensation, under acid catalysis, of 2 to 10 mol, and preferably of 2.5 to 6 mol, of glycidol per mol of alcohol or of alkane-1,2-diol containing 10 to 14 carbon atoms, at a temperature of 50° to 120° C., the glycidol being added slowly to the alcohol or to the alkane-1,2-diol. The preparation of these compounds is described with full details in French Pat. No. 2,169,787.

Among the non-ionic poly(hydroxypropyl ether) surface-active agents described under paragraphs (i), (ii), (iii) and (iv) above, the compounds below are preferred:

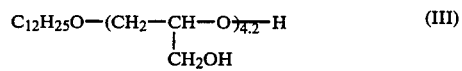

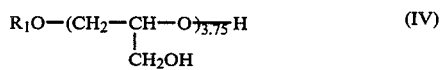

in which $R_1$ denotes a mixture of $C_{10}H_{21}$ and $C_{12}H_{25}$ alkyl radicals;

compounds prepared by the condensation, under alkaline catalysis, of 3.5 mol of glycidol with a mixture of alpha-diols having from 11 to 14 carbon atoms at a temperature of 120°–180° C., by the process described in French Pat. No. 2,091,516 or in U.S. Pat. No. 3,821,372; and

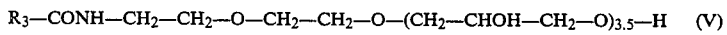

in which $R_3$ denotes a mixture of radicals including the following alkyl and alkenyl radicals: $C_{12}H_{25}$, $C_{14}H_{29}$, radicals derived from copra fatty acids, and the oleyl radical.

The above compounds prepared according to French Pat. No. 2,091,516 or U.S. Pat. No. 3,821,372 with 3.5 mol of glycidol are particularly preferred.

The abovementioned surface-active agents are generally used in the cleaning products for dental, gum and oral care according to the invention at concentrations of between 0.1 and 4% by weight and preferably of between 0.2 and 2% by weight, relative to the total weight of the cleaning products such as toothpastes or mouthwashes.

If the product according to the invention is in the form of a toothpaste, it is generally solid or pastelike.

It generally contains one or more substantially water-insoluble, abrasive polishing agents.

Examples of these polishing agents which may be mentioned are sodium metaphosphate or potassium metaphosphate, tricalcium phosphate, calcium phosphate dihydrate, dicalcium phosphate, calcium pyrophosphate, calcium carbonate, alumina, alumina hydrates and in particular trihydrates, silica, aluminium silicate or zirconium silicate, bentonite and also magnesium orthophosphate or trimagnesium phosphate.

In the case of transparent gels, it will be preferred to use a polishing agent based on colloidal silica or on complex alkali metal aluminosilicates.

The abrasive polishing agent or agents represent 10 to 80% and preferably 15 to 65% of the total weight of the composition.

The cleaning products for dental, gum and oral care according to the invention, referred to below by the abbreviation "cleaning product", can also contain one or more bactericides for combating the formation of dental plaque. These bactericides are generally cationic nitrogen compounds. The following may be mentioned as examples of these cationic compounds: diisobutylphenoxyethoxyethyldimethylbenzylammonium chloride (Hyamine 1622); dodecyltrimethylammonium bromide; dodecyldimethyl(2-phenoxyethyl)ammonium bromide; benzyldimethylstearylammonium chloride; cetylpyridinium chloride; quaternized 5-amino-1,3-bis-(2-ethylhexyl)-5-methylhexahydroxypyrimidine; trimethylcetylammonium bromide; alkyldimethylhydroxyethylammonium bromide (in which alkyl denotes a mixture of radicals derived from copra fatty acids); chlorhexidine; alexidine; and cationic aliphatic tertiary amines.

These bactericides are generally present in a proportion of between 0.005 and 10% and preferably of between 0.05 and 2% by weight, relative to the total weight of the cleaning product.

If the cleaning product is in the form of a toothpaste, it may contain water and it may contain a humectant in a proportion of 10 to 80% of the total weight of the composition. This humectant is advantageously chosen from the group comprising glycerol, sorbitol, propylene glycol or a low molecular weight polyethylene glycol such as polyethylene glycol 400.

The toothpaste can also contain cohesive agents. These are generally natural gums or synthetic thickeners.

Natural gums which may be mentioned are gum tragacanth, xanthane gums and guar, carbo or carragheen gums.

Cellulose derivatives, such as the sodium salt of carboxymethylcellulose, methylcellulose or hydroxyalkylcelluloses, are used essentially as synthetic thickeners.

These cohesive agents can be present in the toothpastes according to the invention in a proportion by weight varying between 0.1 and 10% and preferably between 0.5 and 3%.

The cleaning product according to the invention generally contains a sweetener in a concentration varying in general between 0.1 and 2%, relative to the total weight of the cleaning product. Examples of sweeteners which may be mentioned are sucrose, lactose, fructose, xylitol, sodium cyclamate, maltose and sodium saccharinate.

The cleaning product according to the invention can contain a preservative in a quantity generally of between 0.01 and 0.5%, relative to the total weight of the cleaning product. Examples of preservatives which may be mentioned are compounds such as formaldehyde and its derivatives, methyl parahydroxybenzoate, propyl parahydroxybenzoate and the like.

The cleaning product according to the invention can contain a flavouring substance in a proportion of between 0.5 and 5% by weight, relative to the total weight of the cleaning product. The following may be mentioned as examples of flavouring substances: oils of mint (spearmint or peppermint), aniseed, eucalyptus, cinnamon, clove, sage and liquorice, oils of fruits such as lemon, orange, mandarin and strawberry, or, if appropriate, methyl salicylate.

The pH of the cleaning product according to the invention is usually between 4.5 and 9 and preferably between 5.5 and 8.5.

In the case of a toothpaste, the pH is usually measured for a 20% dispersion of paste in water.

In general, it is necessary to add acidifying agents. Examples of these which may be mentioned are citric acid, benzoic acid, monosodium phosphate and disodium phosphate.

Alkaline pH values are generally used only in the case of toothpastes containing, as the polishing agent, a compound which is unstable in a neutral or acid medium. This is the case, for example, of toothpastes containing calcium carbonate as the polishing agent.

The cleaning products according to the invention advantageously contain an inhibitor of caries. These are carriers of fluoride ions. Examples of the latter which may be mentioned are the following soluble inorganic fluorides: fluorides of sodium, potassium, calcium, ammonium, zinc, tin, copper or barium; fluorosilicates of sodium or ammonium; monofluorophosphates of sodium or aluminium; aluminium difluorophosphate; and sodium fluorozirconate. The fluorine compounds which are most commonly used are sodium fluoride, sodium monofluorophosphate and mixtures thereof.

The fluoride ion carrier is used at a concentration such that the proportion of fluoride ion does not exceed 1500 ppm. By way of example, the concentrations used are between 0.05 and 0.25% for sodium fluoride and these concentrations vary from 0.2 to 0.8% for sodium monofluorophosphate.

The cleaning products according to the invention can also contain other adjuvants normally used in compositions for dental, gum and oral care.

If the cleaning product according to the invention is in the form of a mouthwash, it generally contains, as the vehicle, water or a mixture of water and a lower alcohol containing from 1 to 4 carbon atoms, preferably ethanol, the quantity of lower alcohol being between 5 and 50% and preferably between 20 and 25%, relative to the total weight of the cleaning product.

In the case of mouthwashes, the non-ionic poly(hydroxypropyl ether) surface-active agents preferably represent from 0.1 to 2% by weight, relative to the total weight of the mouthwash.

The mouthwash according to the invention can contain all the constituents mentioned above, with the exception of the polishing agents, which are restricted to toothpastes.

The invention will be illustrated by the non-limiting examples which follow.

EXAMPLE 1

A toothpaste having the following composition is prepared:
Calcium phosphate: 40 g
Glycerol: 24 g
Lactose: 0.3 g
Carragheen/alginate complex sold under the name "Satiagum VZ 40" by CECA-SATIA: 1.5 g
Non-ionic surface-active agent prepared by the condensation, under alkaline catalysis, of 3.5 mol of glycidol with a mixture of alpha-diols having from 11 to 14 carbon atoms, by the process described in French Pat. No. 2,091,516 or in U.S. Pat. No. 3,821,372: 1 g
Diisobutylphenoxyethoxyethyldimethylbenzyl ammonium chloride: 0.25 g
Oil of peppermint: 0.9 g
30% formaldehyde solution: 0.25 g
Water q.s.: 100 g In this toothpaste, the non-ionic surface-active agent gives the product a sufficient foaming power without imparting a bitter taste.

EXAMPLE 2

The following toothpaste is prepared:
Alumina trihydrate: 52 g
70% Sorbitol: 30 g
Fructose: 2 g
Xanthane gum: 1 g
Non-ionic surface-active agent of the formula:

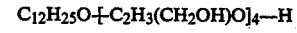

$C_{12}H_{25}O\text{--}[C_2H_3(CH_2OH)O]_4\text{--}H$ 2 g
Chlorhexidine digluconate: 0.06 g
Oil of aniseed: 1.2 g
30% formaldehyde solution: 0.2 g
Titanium oxide: 0.7 g
Water q.s.: 100 g The use of the non-ionic surface-active agent, according to the invention, instead of an anionic surface-active agent such as sodium lauryl-sulphate makes it possible to obtain a toothpaste having a good foaming and cleaning power without adversely affecting the properties imparted by the other constituents.

EXAMPLE 3

The following toothpaste is prepared:
Calcium carbonate: 30 g
70% Sorbitol: 35 g
Non-ionic surface-active agent of the formula:

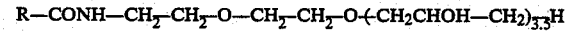

$R\text{--}CONH\text{--}CH_2\text{--}CH_2\text{--}O\text{--}CH_2\text{--}CH_2\text{--}O\text{--}(CH_2CHOH\text{--}CH_2)_{3.3}H$ in which R denotes the following mixture of alkyl and alkenyl radicals: 35% of $C_{12}H_{25}$; 15% of $C_{14}H_{29}$; 15% of oleyl radical; 35% of radicals derived from copra fatty acids: 2 g
Dodecyldimethyl(2-phenoxyethyl)ammonium bromide: 0.4 g
Xylitol: 0.2 g
Methyl parahydroxybenzoate: 0.1 g
Carboxymethylcellulose: 2 g
Oil of liquorice: 0.6 g
Oil of eucalyptus: 0.3 g
Water q.s.: 100 g This toothpaste foams well, it does not have a bitter taste and an anti-plaque agent can easily be incorporated therein.

EXAMPLE 4

The following tooth gel is prepared:

Amorphous synthetic silica having a particle size of 3 microns, sold under the name SYLOID 244 by GRACE: 7 g
Amorphous synthetic silica having a particle size of 8 microns, sold under the name SYLOID AL. I by GRACE: 15 g
Sodium salt of carboxymethylcellulose: 1 g
70% Sorbitol: 65 g
Sodium fluoride: 0.2 g
Non-ionic surface-active agent prepared by the condensation, under alkaline catalysis, of 3.5 mol of glycidol with a mixture of alphadiols having from 11 to 14 carbon atoms, by the process described in French Pat. No. 2,091,516 or in U.S. Pat. No. 3,821,372: 0.8 g
Non-ionic surface-active agent of the formula:

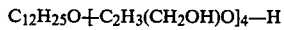

$C_{12}H_{25}O\!\!-\!\![C_2H_3(CH_2OH)O]_4\!\!-\!\!H$ 0.5 g
Dodecyltrimethylammonium bromide: 0.4 g
Oil of lemon: 1.2 g
Yellow colourant (in 1% solution): 0.05 g
Saccharin: 0.3 g
30% formaldehyde solution: 0.25 g
Water q.s.: 100 g This tooth gel composition has a good foaming and cleaning power. Its taste is not unpleasant.

EXAMPLE 5

The following mouthwash is prepared:
Ethanol: 20 g
Glycerol: 8 g
Non-ionic surface-active agent prepared by the condensation, under alkaline catalysis, of 3.5 mol of glycidol with a mixture of alphadiols having from 11 to 14 carbon atoms, by the process described in French Pat. No. 2,091,516 or in U.S. Pat. No. 3,821,372: 2 g
Chlorhexidine digluconate: 0.05 g
Strawberry flavouring: 0.5 g
Water q.s.: 100 g This mouthwash has a good protecting power against agents causing the formation of dental plaque.

EXAMPLE 6

The following toothpaste is prepared:
Calcium phosphate: 30 g
Calcium carbonate: 10 g
Glycerol: 20 g
Carragheen/alginate complex sold under the name "SATIAGUM VZ 40" by CECA-SATIA: 1.6 g
Non-ionic surface-active agent of the formula:

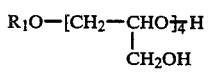

$R_1O\!\!-\!\![CH_2\!\!-\!\!CHO]_{\overline{14}}H$
$\qquad\qquad\qquad |$
$\qquad\qquad\quad CH_2OH$ 0.85 g in which $R_1$ denotes $C_{10}-C_{12}$ alkyl, prepared by the condensation of 4 mol of epichlorohydrin with one mol of Alfol 1012 by the process described in French Pat. No. 1,477,048 or U.S. Pat. No. 3,578,719: 0.85 g
Chlorhexidine digluconate: 0.1 g
Raspberry flavouring: 0.95 g
Titanium oxide: 0.5 g
Methyl parahydroxybenzoate: 0.08 g
Water q.s.: 100 g This toothpaste has a good foaming power.

EXAMPLE 7

The following toothpaste is prepared:
Calcium carbonate: 28 g
Polyethylene glycol 400: 5 g
Propylene glycol: 10 g
Glycerol: 15 g
Sodium salt of carboxymethylcellulose: 1.5 g
Non-ionic surface-active agent of the formula:

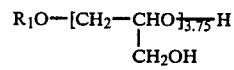

$R_1O\!\!-\!\![CH_2\!\!-\!\!CHO]_{\overline{3.75}}H$
$\qquad\qquad\qquad |$
$\qquad\qquad\quad CH_2OH$ in which $R_1$ denotes $C_{10}-C_{12}$ alkyl, prepared by the condensation of 3.75 mol of epichlorohydrin with one mol of Alfol 1012 by the process described in French Pat. No. 1,477,078 or U.S. Pat. No. 3,578,719: 0.9 g
Dodecyldimethyl(2-phenoxyethyl)ammonium bromide: 0.45 g
Green apple flavouring: 1 g
Water q.s.: 100 g This toothpaste has a good foaming power when the teeth are brushed.

EXAMPLE 8

The toothpaste having the following composition is prepared:
Alumina trihdyrate: 38 g
Calcium phosphate: 11 g
Sorbitol: 20 g
Glycerol: 8 g
Non-ionic surface-active agent prepared by the condensation, under alkaline catalysis, of 3.5 mol of glycidol with a mixture of alpha-diols having from 11 to 14 carbon atoms, by the process described in French Pat. No. 2,091,516 or in U.S. Pat. No. 3,821,372: 1 g
Sodium monofluorophosphate: 0.7 g
Chlorhexidine digluconate: 0.06 g
Mango flavouring: 0.7 g
30% formaldehyde solution: 0.25 g
Water q.s.: 100 g This toothpaste develops a copious foam during brushing.

I claim:

1. A cleaning product for dental, gum and oral care, comprising an effective amount of a non-ionic poly(hydroxypropyl ether) surface-active agent.

2. A cleaning product according to claim 1 comprising an effective amount of a non-ionic poly(hydroxypropyl ether) surface-active agent selected from the group consisting of compounds of formula (i)

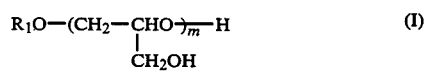

$R_1O\!\!-\!\!(CH_2\!\!-\!\!CHO)_{\overline{m}}\!\!-\!\!H \qquad (I)$
$\qquad\qquad\qquad |$
$\qquad\qquad\quad CH_2OH$ in which $R_1$ denotes an alkyl radical containing 10 to 14 carbon atoms, or a mixture of such alkyl radicals, and m is an integer or decimal number from 2 to 10;

(ii) compounds prepared by the condensation, at 120°–180° C., under alkaline catalysis, of 2 to 10 mol of glycidol with a $C_{10}-C_{14}$ alpha-diol or a mixture of such alpha-diols;

(iii)

$$R_3-CONH-CH_2-CH_2-O-CH_2-CH_2O-(CH_2-CHOH-CH_2-O)_p-H \quad (II)$$

in which $R_3$ denotes an alkyl and/or alkenyl radical having from 11 to 18 carbon atoms, or a mixture of such alkyl and/or alkenyl radicals, and p denotes an integer or decimal number from 1 to 5;

(iv) compounds prepared by the condensation, at 50°–120° C., under acid catalysis, of 2 to 10 mol of glycidol per mol of alcohol or of alkane-1,2-diol containing 10 to 14 carbon atoms;

(v) mixture of above compounds (i) to (iv).

3. A cleaning product according to claim 2 comprising at least one non-ionic poly(hydroxypropyl ether) surface-active agent selected from the group consisting of compounds of formula (i)

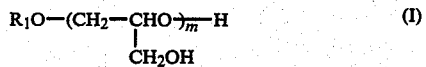

$$R_1O-(CH_2-CHO)_m-H \quad (I)$$
$$\phantom{R_1O-(CH_2-}|$$
$$\phantom{R_1O-(CH_2-}CH_2OH$$

in which $R_1$ denotes an alkyl radical containing 10 to 14 carbon atoms, or a mixture of such alkyl radicals, an m is an integer or decimal number from 3 to 6;

(ii) compounds prepared by the condensation, at 120°–180° C., under alkaline catalysis of 2.5 to 6 mol, of glycidol with a $C_{10}$–$C_{14}$ alpha-diol or a mixture of such alpha-diols;

(iii)

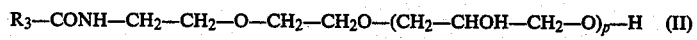

$$R_3-CONH-CH_2-CH_2-O-CH_2-CH_2O-(CH_2-CHOH-CH_2-O)_p-H \quad (II)$$

in which $R_3$ denotes an alkyl and/or alkenyl radical having from 11 to 18 carbon atoms, or a mixture of such alkyl and/or alkenyl radicals, and p denotes an integer or decimal number from 1.5 to 4;

(iv) the compounds prepared by the condensation, at 50°–120° C. under acid catalysis, of 2.5 to 6 mol of glycidol per mol of alcohol or of alkane-1.2-diol containing 10 to 14 carbon atoms;

(v) mixture of above compounds (i) to (iv).

4. A cleaning product according to claim 1 comprising a non-ionic surface-active agent having the formula

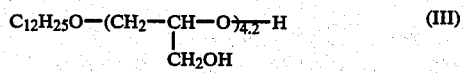

$$C_{12}H_{25}O-(CH_2-CH-O)_{4.2}-H \quad (III)$$
$$\phantom{C_{12}H_{25}O-(CH_2-}|$$
$$\phantom{C_{12}H_{25}O-(CH_2-}CH_2OH$$

or the formula

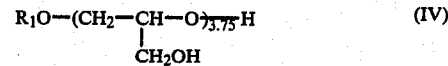

$$R_1O-(CH_2-CH-O)_{3.75}H \quad (IV)$$
$$\phantom{R_1O-(CH_2-}|$$
$$\phantom{R_1O-(CH_2-}CH_2OH$$

in which $R_1$ denotes a mixture of $C_{10}H_{21}$ and $C_{12}H_{25}$ alkyl radicals.

5. A cleaning product according to claim 1 comprising a non-ionic surface-active agent prepared by the condensation, at 120°–180° C., under alkaline catalysis, of 3.5 mol of glycidol with a mixture of alphadiols having from 11 to 14 carbon atoms.

6. A cleaning product according to claim 1 comprising a non-ionic surface-active agent having the formula

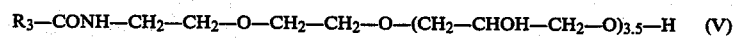

$$R_3-CONH-CH_2-CH_2-O-CH_2-CH_2-O-(CH_2-CHOH-CH_2-O)_{3.5}-H \quad (V)$$

in which $R_3$ denotes a mixture of radicals including the following alkyl and alkenyl radicals: $C_{12}H_{25}$, $C_{14}H_{29}$, radicals derived from copra fatty acids, and the oleyl radical.

7. A cleaning product according to claim 1 comprising from 0.1 to 4% by weight of non-ionic poly(hydroxypropyl ether) surface-active agents.

8. Toothpaste according to claim 7 also comprises 10 to 80% of a polishing agent of appropriate abrasive power.

9. A cleaning product according to claim 7 also comprising from 0.005 to 10% of anti-plaque bactericides.

10. A cleaning product according to claim 7 which further comprises a polishing agent, an anti-plaque and a bactericide.

11. A cleaning product according to claim 10 which further comprises at least one member selected from the group consisting of a cohesive agent, a humectant, a sweetener, a preservative, a flavoring substance, a fluoride ion carrier and other adjuvants normally used in cleaning products for dental, gum and oral care.

12. A mouthwash according to claim 1 comprising 0.1 to 2% by weight of non-ionic poly(hydroxypropyl ether) agent in a vehicle consisting of water or a mixture of water and a lower alcohol having from 1 to 4 carbon atoms (it being possible for the proportion of alcohol to vary between 5 and 50% of the total weight).

13. A mouthwash according to claim 12 also comprising from 0.005 to 10% of anti-plaque bactericides.

14. A mouthwash according to claim 12 also comprising a sweetener, a preservative, a flavouring substance, a fluoride ion carrier.

15. A composition according to claim 1 which is in the form of a toothpaste.

16. A composition according to claim 1 which is in the form of a mouthwash.

* * * * *